US00PP32933P2

(12) United States Plant Patent
Valin

(10) Patent No.: US PP32,933 P2
(45) Date of Patent: Mar. 30, 2021

(54) ***FUCHSIA* PLANT NAMED 'SKYROCKET'**

(50) Latin Name: ***Fuchsia* x *hybrida***
Varietal Denomination: Skyrocket

(71) Applicant: Branded Garden Products Ltd., Southampton (GB)

(72) Inventor: Charles Valin, Ipswich (GB)

(73) Assignee: Branded Garden Products Ltd., Southampton (GB)

( * ) Notice: Subject to any disclaimer, the term of this patent is extended or adjusted under 35 U.S.C. 154(b) by 0 days.

(21) Appl. No.: 16/913,045

(22) Filed: Jun. 26, 2020

(51) Int. Cl.
*A01H 5/02* (2018.01)
*A01H 6/00* (2018.01)

(52) U.S. Cl.
USPC ..... Plt./300

(58) Field of Classification Search
USPC ..... Plt./263.1, 300
See application file for complete search history.

*Primary Examiner* — Susan McCormick Ewoldt
*Assistant Examiner* — Karen M Redden
(74) *Attorney, Agent, or Firm* — Weatherly IP Solutions, LLC; Barbara Campbell

(57) ABSTRACT

A new variety of *Fuchsia* plant named 'Skyrocket' characterized by naturally upright columnar plant habit and bearing pendulous flowers which consist of bright red reflexed sepals above a skirt of white petals with prominent bright red veins, is disclosed.

2 Drawing Sheets

Figure 1:
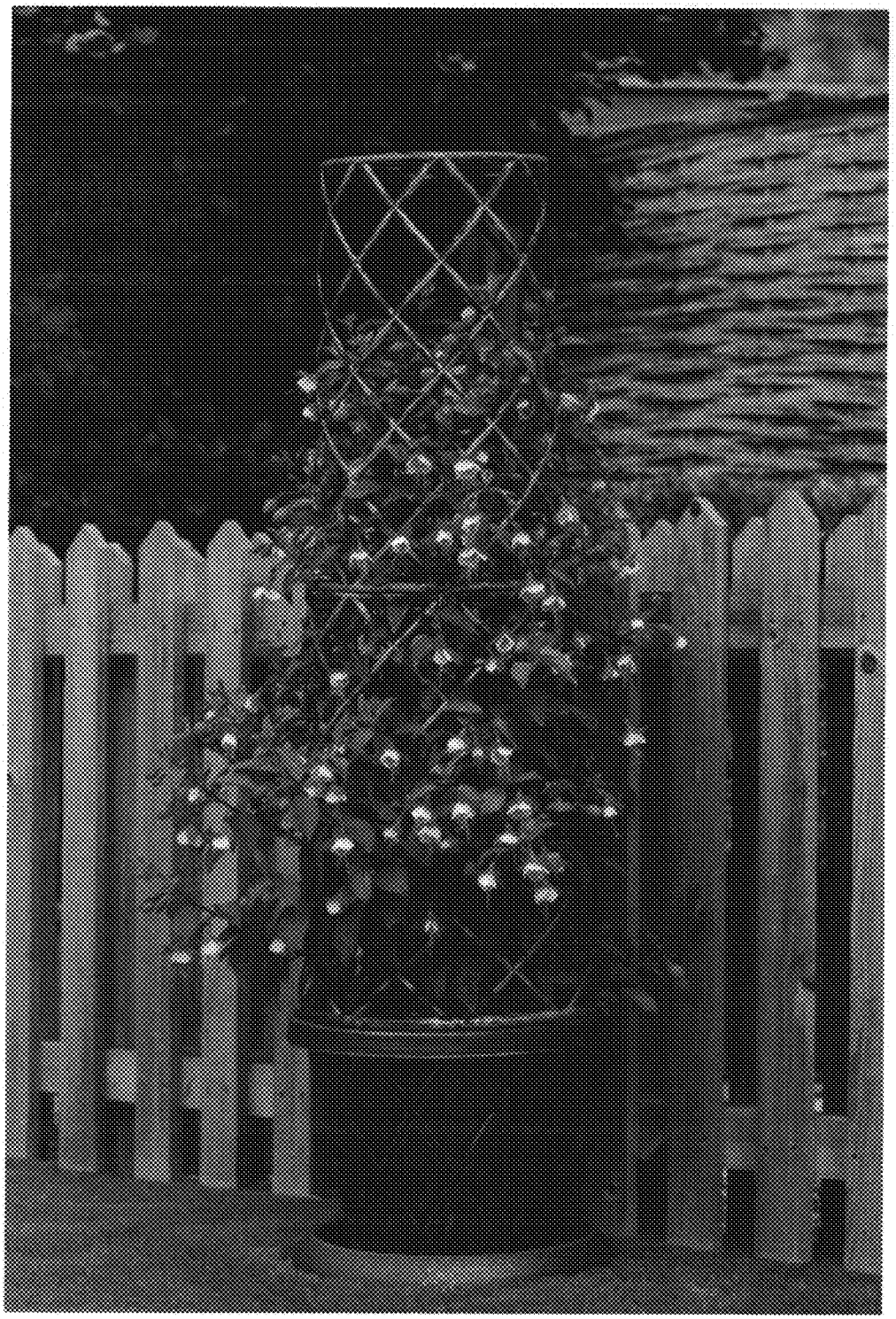

Genus and species: *Fuchsia* x *hybrida*.
Variety denomination: 'Skyrocket'.

BACKGROUND

The present invention relates to a new and distinct variety of *Fuchsia* grown for use as an ornamental for containers and in the landscape. The new variety is known botanically as *Fuchsia* x *hybrida* and will be referred to hereinafter by the variety name 'Skyrocket'.

'Skyrocket' was selected by the inventor in 2012 as a hybrid which resulted from the controlled crossing of seedling parents which the inventor had raised in a *Fuchsia* breeding program commencing in 2006. The objective of the breeding program was to develop new varieties of *Fuchsia* which combine plant hardiness, upright plant habit, vigorous growth and long flowering periods. The breeding program was carried out at a nursery in Ipswich, Suffolk, United Kingdom.

The immediate parents, both male and female, of 'Skyrocket' are two unnamed, unreleased, and unpatented seedlings which the inventor had raised from seed collected from complex hybrids which involved varieties and species of *Fuchsia* which the inventor had chosen with his breeding objectives in mind. As a result, the inventor identifies both parents of 'Skyrocket' as hybrids of (a) *Fuchsia* variety 'Bicentennial' x *Fuchsia* species *regia* subspecies *serrae*, crossed with (b) *Fuchsia* variety 'Dollar Princess' x *Fuchsia* variety 'Lady Boothby'. None of these varieties or the species is patented.

'Skyrocket' was first asexually propagated by the inventor in 2012 using softwood stem cuttings which were rooted and grown on at a nursery in Ipswich, Suffolk, United Kingdom. Since that time, the inventor has determined that 'Skyrocket' is stable and reproduces true to type in successive generations of asexual propagation using softwood stem cuttings.

SUMMARY

The following traits have been repeatedly observed and represent the distinguishing characteristics of the new variety 'Skyrocket'. In combination, these traits set 'Skyrocket' apart from all other varieties of *Fuchsia* known to the inventor. 'Skyrocket' has not been tested under all possible conditions and phenotypic differences may be observed with variations in environmental, climatic and cultural conditions, however, without any variance in genotype.

1. 'Skyrocket' exhibits an upright columnar plant habit.
2. 'Skyrocket' is particularly well suited to production and sale as a columnar form in bud and flower.
3. 'Skyrocket' continues to bear flowers as it grows upward. In its prime condition, 'Skyrocket' bears flowers from top to bottom of the entire plant.
4. The pendulous flowers of 'Skyrocket' consist of bright red reflexed sepals above a single corolla consisting of white petals with prominent bright red veins.
5. 'Skyrocket' is propagated using softwood cuttings.
6. 'Skyrocket' is hardy in USDA Zone 8b and warmer.
7. 'Skyrocket' achieves a height of 60 cm and a diameter of 20 cm to 30 cm after 10 to 15 weeks from planting a rooted cutting.
8. 'Skyrocket' achieves a height of 120 cm and a diameter of 35 cm to 45 cm after 20 to 25 weeks from planting a rooted cutting.

DESCRIPTION OF THE PHOTOGRAPHS

The accompanying color photographs illustrate the overall appearance of the new cultivar 'Skyrocket' showing the colors as true as it is reasonably possible to obtain in colored reproductions of this type. Colors in the photographs may differ from the color values cited in the detailed botanical description, which accurately describe the actual colors of the new variety 'Skyrocket'.

FIG. 1 shows the form of 'Skyrocket' as it may be grown and sold with its characteristic columnar habit and pillar of flowers. Three young plants (rooted cuttings) of 'Skyrocket' have been planted into a 5.5-gallon container in early spring and grown to flowering stage in summer. The drawing has been made from a photograph taken in July 2019 of six-month-old plants growing out of doors in Ipswich, United Kingdom.

Figure 2:
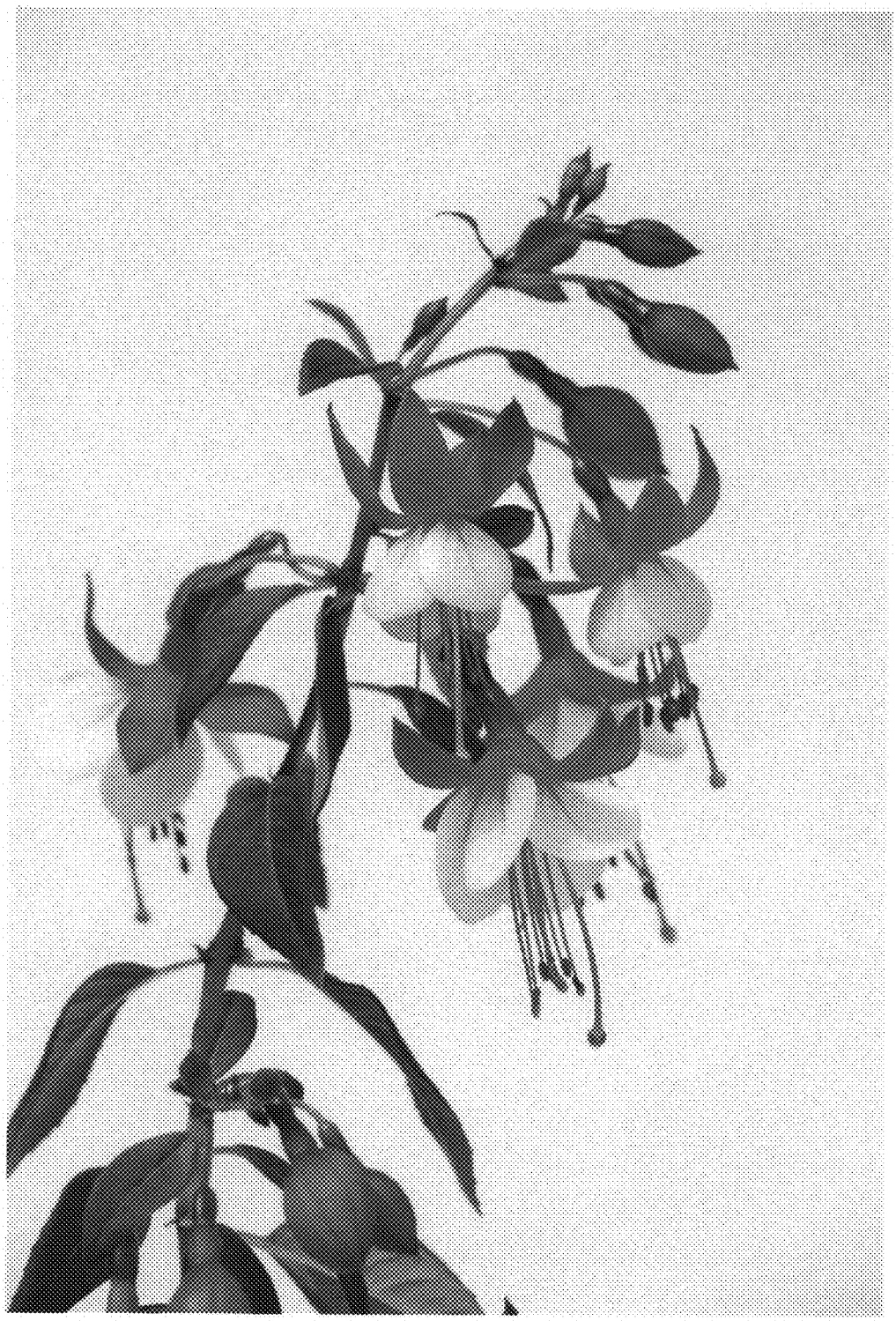

FIG. 2 presents a close-up view of a flowering stem of 'Skyrocket' that is six-months-old and grown outdoors in Oxnard, Calif.

DESCRIPTION OF THE NEW VARIETY

The following is a detailed description of the new *Fuchsia* plant named 'Skyrocket'. Data was collected in Santa Barbara, Calif. in June 2020 from 22-week-old plants which had been grown outdoors in Oxnard, Calif. The color determinations are in accordance with the 2007 Fifth Edition of the Colour Chart of The Royal Horticultural Society, London, England, except where general color terms of ordinary dictionary significance are used. The growing requirements are similar to other *Fuchsia*.

Botanical classification:

*Genus*.—*Fuchsia*.

*Species*.—x *hybrida*.

*Denomination*.—Skyrocket.

*Common name*.—*Fuchsia*.

Parentage:

*Female parent*.—Complex hybrid as follows: (a) *Fuchsia* variety 'Bicentennial' x *Fuchsia* species *regia* subspecies *serrae*, crossed with (b) *Fuchsia* variety 'Dollar Princess' x *Fuchsia* variety 'Lady Boothby'.

*Male parent*.—As female parent, namely complex hybrid as follows: (a) *Fuchsia* variety 'Bicentennial' x *Fuchsia* species *regia* subspecies *serrae*, crossed with (b) *Fuchsia* variety 'Dollar Princess' x *Fuchsia* variety 'Lady Boothby'.

Plant:

*Commercial classification*.—Ornamental.

*Use*.—Container plant for gardens and landscape, and especially well-suited for production as a columnar form in bud and flower.

*Cultural requirements*.—Plant in fertile well-draining soil, in full sun, with regular watering.

*Root system*.—Fine and fibrous.

*Vigor*.—Vigorous.

*Bloom period*.—Late spring to late fall.

*Light requirements*.—Needs 11 to 12 hours of natural daylight for blooming to occur.

*Plant habit*.—Compact and mounding.

*Dimensions*.—60 cm in height, 20 cm to 30 cm. in diameter after 10 to 15 weeks from planting a rooted cutting. 120 cm in height, 35 cm to 45 cm in diameter after 20 to 25 weeks from planting a rooted cutting.

*Hardiness*.—USDA Zone 8b.

*Propagation*.—Propagation is accomplished using softwood cuttings.

*Time to develop roots*.—14 to 21 days are needed for initial cuttings to develop roots.

*Temperature for rooting*.—Recommended air temperature for rooting is 20° Centigrade.

*Crop time*.—Depends on desired finished height. Ranges from 10 weeks for a 60 cm tall plant to 20 to 25 weeks for a 120 cm tall plant in bud and flower.

*Disease susceptibility and resistance*.—There is no specific susceptibility or resistance to disease known to the inventor other than those which are typical for the genus *Fuchsia*.

Stem (below first pinch):

*Dimensions*.—1.5 cm in length, 5 mm in diameter.

*Shape*.—Cylindrical.

*Surface texture*.—Rough, lignified.

*Color*.—N199B.

Branches:

*Number*.—2 primary branches after first pinch, 6 to 8 secondary branches thereafter.

*Arrangement*.—Opposite.

*Dimensions*.—Up to 25 cm in length and 3 mm in diameter.

*Color*.—181B towards base becoming 146C and finally 145A on youngest growth.

*Anthocyanin*.—Present on younger growth (typically latest four internodes), color 181A.

*Surface texture*.—Glabrous, microscopically pubescent.

*Internode length*.—6 cm to 8 cm.

Foliage:

*Shape*.—Elliptic.

*Division*.—Simple.

*Apex*.—Acute.

*Base*.—Cuneate.

*Venation pattern*.—Pinnate.

*Vein color* (*both surfaces*).—145D except midrib adaxial surface which exhibits anthocyanin coloration 181A towards the petiole.

*Margins*.—Minutely dentate, teeth protrusion approximately 0.25 mm, color appears darker green, N137D.

*Arrangement*.—Opposite.

*Leaf surface* (*both surfaces*).—Slightly puberulent.

*Leaf dimensions*.—5.5 cm in length, 2.5 cm in width.

*Leaf attachment*.—Petiolate.

*Petiole shape*.—Sulcate.

*Petiole color*.—145D with anthocyanin coloration 181A on the outward facing surface, approximately around 270 degrees of petiole circumference.

*Petiole dimensions*.—1.5 cm. in length and 1.5 mm. in diameter.

*Leaf color* (*adaxial surface*).—137A.

*Leaf color* (*abaxial surface*).—138B.

*Fragrance*.—None.

Flowers:

*Inflorescence type*.—Solitary.

*Arrangement*.—Two flowers at each node, opposite.

*Aspect*.—Pendulous.

*Shape*.—Calyx consists of sepals which are tightly fused to form green sepal tube which encloses the ovary. Sepal tube becomes bright red (sepals still fused) before sepals become free and reflexed. Petals held beneath reflexed sepals appearing as broad skirt, typically consisting of four overlapping petals, occasionally (approximately one flower in 20) with only three petals (free).

*Persistent or self-cleaning*.—Self-cleaning.

*Aspect*.—Pendulous.

*Buds*.—Quantity: 10 buds on each branch. Shape: Narrowly bulbous, conical apex. Dimensions: 2.5 cm. in length, 1.3 cm in diameter. Color: First forming 53A becoming N57A immediately prior to opening. Surface: Slightly puberulent. Apex: Acute. Base: Rounded.

Sepals:

*Quantity*.—Typically, 4 in number, occasionally (approximately one flower in twenty) 3 in number. Where only 3 sepals present, number of petals also 3 in number.

*Shape*.—Oblanceolate, reflexed.

*Dimensions*.—2.8 cm, in length, 1.3 cm in width.

*Apex*.—Acute.

*Base*.—Truncate.

*Margin*.—Entire.

*Color*.—Where fused, initially (basally) 144A becoming N57A. Where free, N57A with more intensely saturated red longitudinal veins, color still closest to N57A.

Corolla:

*General*.—Consists of four, occasionally three, petals fused at base into very short corolla tube.

*Corolla tube dimensions*.—4 mm in depth, 3 mm in diameter.

*Corolla tube color*.—157C.

*Petals*.—Quantity: 4, occasionally (approximately one flower in twenty) 3, as with sepals. Arrangement: Four petals overlapping, three petals free. Appear as inverted cup with strongly exerted stamens and pistil. Shape: Very broadly elliptic. Dimensions: 22 mm in length, 20 mm in width. Apex: Rounded. Base: Cuneate. Margin: Entire. Surface texture: Glabrous Color: White, whiter than NN155D, with clear pinnate veining N57A.

*Peduncle*.—Shape: Cylindrical. Dimensions: 3 cm to 6 cm in length, 1.0 mm to 1.25 mm in diameter. Color: 145A. Surface texture: Glabrous.

*Flower fragrance*.—None observed.

Reproductive organs:

*Stamens*.—Quantity: Eight (where four petals, four sepals); six (where three petals, three sepals). Color: N57A. Dimensions: 3.5 cm to 4.0 cm in length and 0.75 mm in diameter.

*Anthers*.—Shape: Ellipsoid, bifid, dorsifixed. Dimensions: 2.5 mm in length, 1.5 mm in width. Color: Initially 153A becoming 187A. Pollen: None.

*Pistil*.—Shape: Narrow and long cylindrical. Dimensions: 4.3 cm in length, 1.25 mm in width. Color: N57A. Surface: Very lightly pubescent.

*Stigma*.—Shape: Globular. Dimensions: 3 mm in diameter. Color: N57A.

*Ovary*.—Shape: Cylindrical with rounded ends, as capsule. Position: Inferior. Dimensions: 8 mm in length, 5 mm in diameter. Color: 144A.

*Fruit and seed production*.—None observed. Dissected ovary contains numerous (more than 100) tiny unfertilized ovules.

COMPARISON WITH PARENTAL LINES AND KNOWN VARIETY

'Skyrocket' can be compared with the varieties and species involved in its complex hybrid parents by plant habit and by flower appearance namely sepal color, corolla petal arrangement (single or double) and corolla petal color.

'Skyrocket' grows with an upright plant habit and bears flowers with bright red sepals and single corolla of white petals with bright red veins.

*Fuchsia* 'Bicentennial' grows with a pendulous plant habit and bears flowers with pink sepals and double corolla of orange-red petals.

*Fuchsia regia* ssp. *serrae* is a naturally climbing species with narrow leaves and bears slender flowers with red sepals and single corolla of purple petals.

*Fuchsia* 'Dollar Princess" grows with a pendulous plant habit and bears flowers with red sepals and double corolla of dark purple petals.

*Fuchsia* 'Lady Boothby' grows with an upright habit and bears flowers with red sepals and single corolla of dark purple petals.

The variety of *Fuchsia* which the inventor considers to most-closely resemble 'Skyrocket' is *Fuchsia* Plant Named 'Kiefulap' (U.S. Plant Pat. No. 13,772). Whereas 'Kiefulap' and 'Skyrocket' both bear flowers with red sepals and white petals, the plant habits of the two varieties are distinctly different. 'Kiefulap' achieves a greater width than height whereas 'Skyrocket' is significantly taller than wider. As each plant continues to grow, this difference in proportion increases. 'Skyrocket' will achieve twice the height of 'Kiefulap' with a similar plant diameter.

I claim:

1. A new and distinct variety of *Fuchsia* plant named 'Skyrocket' as described and illustrated herein.

* * * * *